(12) United States Patent
Emslie et al.

(10) Patent No.: US 7,347,990 B2
(45) Date of Patent: *Mar. 25, 2008

(54) STICK COMPOSITIONS

(75) Inventors: Bruce Steven Emslie, Wirral (GB);
Kevin Ronald Franklin, Wirral (GB);
Martin Peter Cropper, Wirral (GB)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 746 days.

This patent is subject to a terminal disclaimer.

(21) Appl. No.: 10/842,094

(22) Filed: May 10, 2004

(65) Prior Publication Data

US 2004/0223994 A1 Nov. 11, 2004

(30) Foreign Application Priority Data

May 10, 2003 (GB) .................................. 0310767.9

(51) Int. Cl.
*A61Q 15/00* (2006.01)
*A61K 8/02* (2006.01)

(52) U.S. Cl. .................... 424/65; 424/400; 424/401

(58) Field of Classification Search ................. 424/65, 424/400, 401
See application file for complete search history.

(56) References Cited

U.S. PATENT DOCUMENTS

| | | | |
|---|---|---|---|
| 3,969,087 A | 7/1976 | Saito et al. ........................ 44/7 |
| 5,429,816 A | 7/1995 | Hofrichter et al. ............ 424/66 |
| 5,650,144 A | 7/1997 | Hofrichter et al. ............ 424/66 |
| 5,840,286 A | 11/1998 | Gardlik et al. ................ 424/65 |
| 5,840,287 A | 11/1998 | Guskey et al. ................ 424/65 |
| 6,241,976 B1 | 6/2001 | Esser et al. ..................... 424/65 |
| 6,287,544 B1 | 9/2001 | Franklin et al. ............... 424/65 |
| 2002/0159961 A1 | 10/2002 | Yamato et al. ................ 424/65 |

FOREIGN PATENT DOCUMENTS

| WO | 93/23008 | 11/1993 |
|---|---|---|
| WO | 2003/005977 | 1/2003 |

OTHER PUBLICATIONS

Co-pending application: Applicant: Emslie et al. U.S. Appl. No. 10/842,136, filed May 10, 2004.
Co-pending application: Applicant: Franklin et al. U.S. Appl. No. 10/842,137, filed May 10, 2004.
PCT International Search Report in a PCT application PCT/EP 2004/004507.
GB Search Report in a GB application GB 0310771.1.
PCT International Search Report in a PCT application PCT/EP 2004/004512.

*Primary Examiner*—Shelley A. Dodson
(74) *Attorney, Agent, or Firm*—Karen E. Klumas

(57) ABSTRACT

Many cosmetic stick compositions containing a continuous phase of a water-immiscible cosmetic oil structured by a fibre-forming amido structurant and an active cosmetic ingredient either exhibit poor physical stability when formed, or cannot be made readily using conventional processes for making stick compositions. The problem can be ameliorated or overcome by the use of a combination of amido structurants comprising in class (i) an N-acylaminoacid amide in which the N-acyl substituent has the formula —CO—$R^x$ in which $R^x$ represents a branched $C_6$ to $C_{11}$ alkyl group in combination with a further amido structurant, (class (ii), including a polyamido-substituted cyclohexane, an amido derivative of di or tricarboxylic acids or an hydroxystearamide and particularly employing an N-acylaminoacid amide in which the N-acyl substituent contains a linear alkyl group, or a cyclodipeptide.

74 Claims, No Drawings

STICK COMPOSITIONS

The present invention relates to stick compositions and in particular to such compositions containing a cosmetic active, a carrier material comprising a cosmetically acceptable water-immiscible oil that is solidified by an amido-substituted amino acid and to their preparation and use. Especially, the present invention relates to such compositions in emulsion form.

TECHNICAL FIELD

Background and Prior Art

Cosmetic formulations are known and available to the public in several different physical forms for application using the corresponding type of applicator, including dispensers for powder mixes, foams, gelled or thickened liquids, liquids of low viscosity that can be sprayed, aerosol formulations, creams, soft solids and sticks. The preferred choice of physical form can often depend on the history of product, and local preferences, which may themselves vary over time as fashions change. One physical form, which is commonly employed for lipsticks and has been popular especially in North America for antiperspirant and deodorant compositions during the last twenty years is that of sticks. The term "stick" herein is employed in its natural meaning, that is to say a material that is firm to the touch, is often in the shape of a rod or bar and commonly is housed in a container comprising a barrel having an open end and an opposed piston which can be slid up the barrel to expel the stick, which retains its shape and integrity during its expulsion.

Cosmetic sticks typically comprise a cosmetic active that is dissolved or suspended in a cosmetically acceptable carrier material of which at least a fraction is a cosmetically acceptable water-immiscible oil. Where the composition also includes a polar carrier material such as water and/or a water-miscible mono or polyhydric alcohol, the composition adopts the form of an emulsion. These can adopt the form of water-in-oil or oil-in-water emulsions. The former arrangement is often preferred by users of cosmetic products because the product is normally brought into topical contact with skin and in a water-in-oil emulsion, it is the oil phase that is the first to make contact. In order to form a stick, it is often necessary to solidify the external, continuous phase of the emulsion, such as the oil phase.

One class of material that has hitherto been proposed for solidifying water-immiscible oils comprises non-polymeric fibre-forming structurants. A number of such structurants comprise alkyl ester derivatives of certain saccharides, such as maltose or particularly cellobiose, and others comprise N-acyl amido derivatives of aminoacids, di- or tri-carboxylic acids or cyclohexane. The present invention is directed particularly to water in oil emulsions in which a continuous phase comprising a water-immiscible oil is solidified with one or more N-acyl amido derivatives of aminoacids. Water-in-oil emulsions in which an oil phase is solidified with a fibre-forming structurant have been described in U.S. Pat. No. 6,241,976 and U.S. Pat. No. 6,287,544.

Many N-acyl amido derivatives of aminoacids that are suitable for solidifying cosmetically-acceptable oils to a greater or lesser extent have been described by Ajinomoto Co Ltd in U.S. Pat. No. 3,969,087, including in particular derivatives of glutamic acid or aspartic acid. The derivative disclosed therein that was apparently the most preferred by Ajinomoto was N-lauroylglutamic acid, -di-n-butylamide, as indicated by the fact that for many years it was the only such material that was commercially available from them (trade name GP-1). Research into the preparation of emulsion sticks described in U.S. Pat. No. 6,241,976 or U.S. Pat. No. 6,287,544 indicated that GP-1 structurant was not suitable for the structuring of emulsion sticks. Although sufficient GP-1 could be incorporated into an oil phase to solidify it, the resultant emulsion was not storage stable, even at ambient temperature. Within a matter of a few days, the structure became impaired with the result that it became unacceptably soft and waxy, and left a thick, sticky and greasy film when applied to skin that was disliked by consumers. Additionally, clear formulations become cloudy or opaque.

More recently, in USA-2002/0159961, Ajinomoto has described a selection of N-acyl amido derivatives of aminoacids from within the overall ranges described in U.S. Pat. No. 3,969,087. In this selection, the alkyl group $R^3$ in the N-acyl substituent —CO—$R^3$ is characterised by containing from 7 to 10 carbon atoms, and may be branched. The '961 specification discloses that the new selection of aminoacid derivatives can be employed to gel non-polar organic liquids, including water-in oil emulsions containing less than 50% water. Although the specification includes worked examples of non-polar liquids gelled with the newly selected aminoacid derivatives, there is no worked example of an emulsion being gelled, let alone an antiperspirant emulsion. In the course of research which led to the present invention, attempts were made to prepare water-in-oil emulsions containing a cosmetic active constituent using a representative example of the newly selected aminoacid derivatives as structurant. It was found that the solubility/gelling against temperature profiles of the material in cosmetic oils meant that it was not possible to obtain an emulsion solid using current processing techniques known and described in, for example, U.S. Pat. No. 6,241,976. This was because the gelation temperature was too high, above the boiling point of water.

SUMMARY OF THE INVENTION

It is an object of the present invention to avoid or at least ameliorate one or more of the difficulties or disadvantages indicated hereinabove in the preparation of solidified emulsions containing a cosmetic active ingredient.

According to one aspect of the present invention, there is provided a cosmetic composition as described hereinafter in claim 1.

By the employment of the combination of fibre-forming structurants described herein, it is possible to prepare cosmetic sticks of improved storage stability.

According to a second aspect of the present invention, there is provided a process for the preparation of a cosmetic composition according to the first aspect. A particular process is described in claim 71 herein.

According to a third aspect of the present invention there is provided a cosmetic method for inhibiting or controlling perspiration and/or body malodours by the topical application to skin of an effective amount of a composition according to the first aspect.

DETAILED DESCRIPTION OF THE INVENTION AND PREFERRED EMBODIMENTS THEREOF

The present invention relates to emulsions containing a cosmetic active ingredient in which the continuous phase is water-immiscible and is solidified using a mixture of at least two classes of fibre-forming structurants containing an amido linkage of which one class is gellant (i) an N-acyl aminoacid amide, the acyl group containing a branched alkyl group of 4 to 12 carbon atoms. Herein, it is considered that cyclic dipeptides contain an amido linkage.

Gellant (i)

Gellant (i) is an N-acyl aminoacid amide that satisfies general formula (1) $A^x$—CO—$R^x$ in which $A^x$ represents the residue of an amino acid amide and $R^x$ represents a branched alkyl group containing from 4 to 12 carbon atoms and sometimes 7 to 10 carbon atoms. In many instances, the aminoacid amide residue $A^x$ can be represented by formula (2)

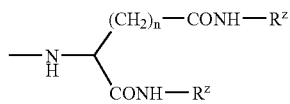

in which n represents an integer of 1 or 2 and $R^z$ represents an alkyl group, which can be linear or branched, containing from 1 to 10 and particularly from 3 to 5 carbon atoms, each of which $R^z$ groups can be the same or different.

Accordingly, the amino acid from which such an amide residue $A^x$ is derivable is glutamic or aspartic acid. In some especially preferred embodiments, each $R^z$ represents a butyl group, especially an n-butyl group, and particularly in the derivative of glutamic acid, which residue is represented by formula (3)

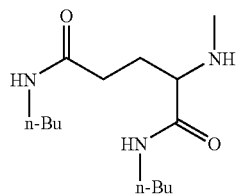

In formula (1), $R^x$ preferably represents an alkyl group containing either one or two or possibly three side chains, such as particularly one side chain. Desirably, any side chain in $R^x$ contains from 1 to 4 carbon atoms, such as methyl, ethyl propyl or butyl, and often from 1 to 3 carbon atoms, of which ethyl is very convenient. The alkyl backbone preferably contains from 4 to 8 carbon atoms and often from 4 to 7 carbon atoms. The location of the side chain along the alkyl group backbone is at the discretion of the producer, of which the 2 position is often favoured. An especially desirable branched chain group for $R^x$ is 1-ethylpentyl, so that the resultant acyl group is 2-ethylhexanoyl. Other branched chain groups for $R^x$ include 1-methylbutyl, isobutyl and 1-butylheptyl. It is particularly desirable to employ a gellant (i) in which $R^x$ is according to one or more of the branched alkyl groups named above and the amide residue is derived from glutamic acid dibutylamide.

The weight proportion of gellant (i) in the composition is commonly selected in the range of 1 to 8% and in many desirable embodiments is at least 1.5% w/w. It is often unnecessary to employ more than 6% w/w of gellant (i) in the composition. The proportion of gellant in the composition can also be determined by relation to the water-immiscible phase which it is structuring. The weight proportion of gellant (i) is usually selected in the range of from 2 to 15% w/w of the water-immiscible phase and is often present in a proportion of at least 3% w/w of that phase. Its weight proportion of that phase in a number of preferred embodiments is up to 11%. The weight proportion of each gellant in the composition or water-immiscible phase will often be selected in concert with the choice of co-gellant or gellants, the weight of co-gellant or gellants and the desired hardness of the stick.

Gellant (i) is employed in conjunction with a second amide-fibre-forming structurant, gellant (ii). Within such second amide fibre-forming structurants are included gellant (iia) namely N-acyl aminoacid amides other than the branched-chain substituted N-acyl aminoacid amides of gellant (i), gellant (iib) cyclodipeptides, gellant (iic) diamido or triamido substituted cyclohexane and gellant (iid), amide derivatives of di and tribasic carboxylic acids and gellant (iie) namely hydroxystearic acid amides. One or more of gellants (iia) to (iid) can be employed simultaneously.

N-acyl aminoacid amides according to gellant (iia) are described in U.S. Pat. No. 3,969,087. A list of many of such amides and the general method of manufacture are described in said patent specification in column 1 line 63 to column 4 line 47, and specific amido derivatives are named in Example 1 in column 6 to 8, which passages from the text are incorporated herein by reference. Herein, gellant (iia) often satisfies formula (4) $A^y$-CO—$R^y$ in which $A^y$ represents an amino acid amide and $R^y$ represents a linear alkyl group containing from 9 to 21 carbon atoms. Highly desirably, $A^y$ represents an amino acid amide residue in accordance with the formula (5)

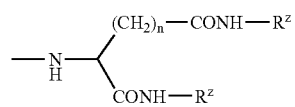

in which n represents an integer of 1 or 2 and $R^z$ represents an alkyl group, which can be linear or branched, containing from 1 to 10 and particularly from 3 to 5 carbon atoms, each of which $R^z$ groups can be the same or different. Accordingly, the amino acid from which such an amide residue $A^y$ is derivable is glutamic or aspartic acid. In some especially preferred embodiments, each $R^z$ represents a butyl group, especially an n-butyl group, and particularly in the derivative of glutamic acid. Such a particularly preferred residue $A^y$ is likewise represented by formula (3) given supra for residue $A^x$.

In formula (4), $R^y$ often contains from 9 to 15 linear carbons, of which one preferred group comprises undecyl. N-Lauroyl-L-glutamic acid di-n-butylamide, formula (6)

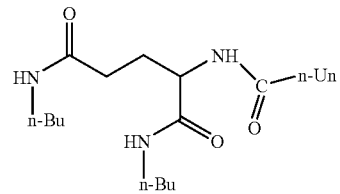

(n-Un=undecyl) employed in Example 14 of '087, is an especially desirable amide structurant for employment in the instant invention compositions and is commercially available from Ajinomoto under their trade designation GP-1.

Herein, the weight proportion of gellant (iia) in the composition is commonly selected in the range of 1 to 8% and in many desirable embodiments is at least 1.5% w/w. It is often unnecessary to employ more than 6% w/w of gellant (i) in the composition. The proportion of gellant in the composition can also be determined by relation to the water-immiscible phase which it is structuring. The weight proportion of gellant (iia) is usually selected in the range of from 2 to 15% w/w of the water-immiscible phase and is often present in a proportion of at least 3% w/w of that phase. Its weight proportion of that phase in a number of preferred embodiments is up to 11%. The weight proportion of the gellant in the composition or water-immiscible phase will often be selected in concert with the choice of co-gellant or gellants, the weight of co-gellant or gellants and the desired hardness of the stick.

The weight ratio of gellant (i) to gellant (iia) is often selected in the range of from 3:1 to 1:3. In many instance the weight ratio is no higher than 2:1 and in such or other instances, the weight ratio is at least 1:2. A convenient weight ratio can be in the range of 1.1:1 to 1:1.1.

The combined weight proportion of gellants (i) and (iia) in the composition is often selected in the range of from 4 to 12% and in some well desired embodiments from 5 to 9%. When expressed in terms of the weight proportion of the two gellants in the water-immiscible phase, this is often from 8 to 22% w/w of the phase and in many desirable embodiments from 10 to 17% w/w.

A second sub-class of amide gellants (iib) suitable for employment in the instant invention comprises structurants which satisfy the following general formula (7):—

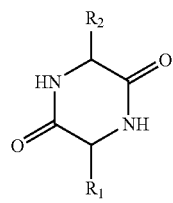

in which one of $R_1$ and $R_2$ represents an alkyl, alkyl ester group and the other represents an alkyl or alkaryl group. Examples of such amides are described in two papers by Hanabusa et al, entitled respectively Cyclo(dipeptide)s as low molecular-mass Gelling Agents to harden Organic Fluids, J. Chem Soc. Commun., 1994 pp 1401/2, and Low Molecular Weight Gelators for Organic Fluids: Gelation using a Family of Cyclo(dipeptide)s, in the Journal of Colloid and Interface Science 224, 231-244 (2000), which descriptions of amide structurants are incorporated herein by reference.

However, it is especially preferred to employ herein a sub-class of cyclodipeptides not expressly disclosed by Hanabusa, which sub-class satisfies the general formula (8):—

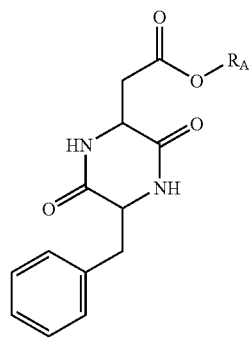

in which $R_A$ represents a carbocyclic or heterocyclic group containing not more than 2 rings. Such materials are sometimes herein referred to as DOPA derivatives.

In DOPA derivatives, $R_A$ can comprise two fused rings, but preferably comprises a single six membered ring, either carbocyclic or heterocyclic, or a bridged ring. When A is carbocylic, it can be either saturated or unsaturated, preferably unsaturated or aromatic. When $R_A$ is heterocyclic, it is preferably saturated.

Although the cyclic group within $R_A$ can be unsubstituted, it is preferably substituted by at least one alkyl substituent, which preferably contains no more that 16 carbon atoms. In some highly desirable embodiments the alkyl substituent has a longest chain length of up to 4 carbon atoms, and in certain or those a total carbon content of up to 5 carbon atoms. The alkyl substituent may be linear or branched. Preferred examples include methyl, ethyl, propyl, isopropyl, butyl isobutyl or t-butyl or isopentyl. In a number of very suitable DOPA derivatives, $R_A$ contains two or more alkyl substituents and especially those selected from the above list of preferred examples. The alkyl substituents may be the same, such as two or more methyl substituents, or may be a combination of different substituents such as a methyl and isopropyl substituents. When $R_A$ is saturated, the substituents may depend from the same carbon atom in the ring, such as two methyl groups, or from different carbon atoms. In several highly desirable derivatives, two alkyl substituents are meta or para to each other, for example meta methyl groups or a para methyl and isopropyl group. In yet other derivatives, the ring may include a methylene bridge, which preferably likewise completes a six membered ring.

In some suitable DOPA derivatives, the or one alkyl substituent may be ortho or para to the bond with the DOPA residue, as in 4-methyl-phenyl-. In some or other DOPA derivatives, the bond with the DOPA residue is meta to one or preferably two methyl substituents.

When $R_A$ is heterocyclic, the heterocyclic atom is suitably nitrogen. Conveniently, the heterocyclic atom can be para to the bond with the DOPA residue. Moreover, in a number of desirable derivatives, the heteroatom is ortho to at least one alkyl group, better in a saturated ring and especially to up to 4 ortho methyl groups.

The group $R_A$ is often most easily referred to as the residue from the corresponding alcohol which may be reacted with DOPA to form the ester linkage. Thus, desirable examples of $R_A$ include the residues from 4-alkyl phenol, such as 4-nonyl-phenol, and 2,6-dialkyl- or 2,2,6,6-tetraalkyl-4-piperidinol, such as 2,2,6,6-tetramethyl-4-piperidinol.

In some preferred DOPA derivatives, the ring in $R_A$ is carbocyclic, and is substituted by at least two alkyl groups of which at least one is methyl and the other or one of the others is isopropyl. Examples of such preferred $R_A$ residues include menthol, isopinocamphenol and 3,5-dialkyl cyclohexanol such as 3,5-dimethyl cyclohexanol. Especially preferred $R_A$ residues include thymol. Yet others include the DOPA derivatives from carveol and carvacrol.

The DOPA derivatives used in this invention may be a mixture of compounds within the general formulae given, or may be a single compound.

The DOPA derivatives can be prepared by reacting the respective alcohol with DOPA in acid form (DOPAA), or possibly with an acid chloride, or possibly an anhydride or an ester containing a DOPA residue. DOPAA can be obtained by cyclising aspartame. DOPAA can be reacted with the relevant alcohol of formula $R_AOH$, preferably in a mole ratio to the DOPAA of at least 2:1 in dimethyl sulphoxide, in a ratio of from 6:1 to 12:1, in the presence of a promoter, such as a carbonyldiimidazole, in an amount preferably from 0.5 to 2 moles of promoter per mole of DOPA acid. The reaction is conveniently carried out at a temperature from 40 to 60° C.

The weight proportion of gellant (iib) in the composition is commonly selected in the range of 0.4 to 4% and in many desirable embodiments is at least 0.6% w/w. It is often unnecessary to employ more than 2% w/w of gellant (iib) in the composition. The proportion of gellant in the composition can also be determined by relation to the water-immiscible phase which it is structuring. The weight proportion of gellant (iib) is usually selected in the range of from 0.8 to 7.5% w/w of the water-immiscible phase and is often present in a proportion of at least 1.2% w/w of that phase. Its weight proportion of that phase in a number of preferred embodiments is up to 3.75%.

The weight ratio of gellant (i) to gellant (iib) is often selected in the range of from 1:1 to 5:1. In many instances the weight ratio is no higher than 4:1 and commonly up to 3:1. In such or other instances, the weight ratio is advantageously at least 1.5:1. A convenient weight ratio can be in the range of 1.5:1 to 2.5:1.

The combined weight proportion of gellants (i) and (iib) in the composition is often selected in the range of from 1.5 to 10% and in some well desired embodiments from 2 to 6%. When expressed in terms of the weight proportion of the two gellants in the water-immiscible phase, this is often from 3 to 19% w/w of the phase and in many desirable embodiments from 4 to 11% w/w.

The amido-substituted fibre-forming structurants (ii) are especially desirably selected from sub-classes (iia) and (iib) described above. Subsequently described sub-classes (iic), (iid) and (iie) are particularly desirably employed in conjunction with either or both of classes (iia) or (iib), often representing a minor fraction of the total weight of all of structurants (ii) in the composition.

A third sub-class of amido-substituted fibre-forming structurants, (iic) comprises di-amido and triamido-substituted cyclohexane. Particular sub-classes of such compounds comprise -1,2 or -1,3 substituted cyclohexane compounds, and 1,3,5-triamido-substituted cyclohexane in which the amido group desirably accords with the general formula —$(CH_2)_v$—CO—NH—$R^{111}$ and —$(CH_2)_v$—NH—CO—$R^{111}$) in which $R^{111}$ represents an alkyl group of from 5 to 27 carbon atoms and v is an integer selected from zero and one.

When the cyclohexane ring is substituted by two amido substituents, the substituents preferably satisfy —$(CH_2)_v$—NH—CO—$R^{111}$) and are very desirably in the 1,2 or 1,3 positions relative to each other around the cyclohexane nucleus. When they are in the 1,3 relative positions, v preferably represents 1. When the two substituents are in the 1,2 relative position, v preferably is zero.

When the cyclohexane ring is substituted by three amido groups, they each preferably satisfy —$(CH_2)_v$—CO—NH—$R^{111}$.

$R^{111}$ can be linear or branched. Preferably the number of carbons in $R^{111}$ is selected in the range of 8 to 20. For example undecyl, dodecyl, 2-ethylhexyl, octadecyl, or dimethyloctyl.

Herein, the weight proportion of gellant (iic) in the composition is commonly selected in the range of 1 to 8% and in many desirable embodiments is at least 1.5% w/w. It is often unnecessary to employ more than 6% w/w of gellant (i) in the composition. The proportion of gellant in the composition can also be determined by relation to the water-immiscible phase which it is structuring. The weight proportion of gellant (iic) is usually selected in the range of from 2 to 15% w/w of the water-immiscible phase and is often present in a proportion of at least 3% w/w of that phase. Its weight proportion of that phase in a number of preferred embodiments is up to 11%. The weight proportion of the gellant in the composition or water-immiscible phase will often be selected in concert with the choice of co-gellant or gellants, the weight of co-gellant or gellants and the desired hardness of the stick.

The weight ratio of gellant (i) to gellant (iic) is often selected in the range of from 3:1 to 1:3. In many instance the weight ratio is no higher than 2:1 and in such or other instances, the weight ratio is at least 1:2.

The combined weight proportion of gellants (i) and (iic) in the composition is often selected in the range of from 4 to 12% and in some well desired embodiments from 5 to 9%. When expressed in terms of the weight proportion of the two gellants in the water-immiscible phase, this is often from 8 to 22% w/w of the phase and in many desirable embodiments from 10 to 17% w/w.

A fourth sub-class of amide structurants suitable for employment herein, gellant (iid) comprises amide derivatives of di and tribasic carboxylic acids. Such gellants can be in accordance with the description either as set forth in U.S. Pat. No. 5,840,288 and specifically the passage from column 12 line 37 to column 14 line 20 or as set forth in U.S. Pat. No. 6,190,673B1, specifically the passages col 1 line 47 to col 2 line 38 and col 3 line 47 to col 5 line 23. Their general methods of manufacture are as described in the passage in U.S. Pat. No. 5,840,288 in column 12 line 37 to 39 or as set forth in U.S. Pat. No. 6,190,673B1, in the passage in col 5 lines 28 to 43. Specific suitable gellants (iid) are listed in column 13 line 62 to column 14 line 7 in U.S. Pat. No. 5,840,288 and in Table 1 in col 13 of U.S. Pat. No. 6,190,673B1. Convenient carboxylic acid for the preparation of amide derivatives include succinic acid and aliphatic acids containing three vicinal carboxylic acid groups such as 1-propene-trioic acid. Each amide substituent preferably contains an alkyl, especially linear alkyl group of from 3 to 12 carbons. A particularly preferred gellant (iid) is 2-dodecyl-N,N'-dibutylsuccinamide or 1-propene-1,2,3-trioctylamide or 2-hydroxy-1,2,3-propane-tributylamide. Such passages are incorporated herein by reference.

Herein, the weight proportion of gellant (iid) in the composition is commonly selected in the range of 1 to 8% and in many desirable embodiments is at least 1.5% w/w. It is often unnecessary to employ more than 6% w/w of gellant (i) in the composition. The proportion of gellant in the composition can also be determined by relation to the water-immiscible phase which it is structuring. The weight proportion of gellant (iid) is usually selected in the range of from 2 to 15% w/w of the water-immiscible phase and is often present in a proportion of at least 3% w/w of that phase. Its weight proportion of that phase in a number of preferred embodiments is up to 11%. The weight proportion of the gellant in the composition or water-immiscible phase will often be selected in concert with the choice of co-gellant or gellants, the weight of co-gellant or gellants and the desired hardness of the stick.

The weight ratio of gellant (i) to gellant (iid) is often selected in the range of from 3:1 to 1:3. In many instance the weight ratio is no higher than 2:1 and in such or other instances, the weight ratio is at least 1:2.

The combined weight proportion of gellants (i) and (iid) in the composition is often selected in the range of from 4 to 12% and in some well desired embodiments from 5 to 9%.

When expressed in terms of the weight proportion of the two gellants in the water-immiscible phase, this is often from 8 to 22% w/w of the phase and in many desirable embodiments from 10 to 17% w/w.

A fifth alternative sub-class (iie) of amido gellants within gellant (ii) comprises hydroxystearamides and in particular 12-hydroxy-stearamides. The amido substituent in such amides preferably contains an alkyl, particularly a linear alkyl group between 3 and 13 carbon atoms, such as propyl, butyl, heptyl or undecanyl.

Herein, the weight proportion of gellant (iie) in the composition is commonly selected in the range of 1 to 8% and in many desirable embodiments is at least 1.5% w/w. It is often unnecessary to employ more than 6% w/w of gellant (i) in the composition. The proportion of gellant in the composition can also be determined by relation to the water-immiscible phase which it is structuring. The weight proportion of gellant (iie) is usually selected in the range of from 2 to 15% w/w of the water-immiscible phase and is often present in a proportion of at least 3% w/w of that phase. Its weight proportion of that phase in a number of preferred embodiments is up to 11%. The weight proportion of the gellant in the composition or water-immiscible phase will often be selected in concert with the choice of co-gellant or gellants, the weight of co-gellant or gellants and the desired hardness of the stick.

The weight ratio of gellant (i) to gellant (iie) is often selected in the range of from 3:1 to 1:3. In many instance the weight ratio is no higher than 2:1 and in such or other instances, the weight ratio is at least 1:2.

The combined weight proportion of gellants (i) and (iie) in the composition is often selected in the range of from 4 to 12% and in some well desired embodiments from 5 to 9%. When expressed in terms of the weight proportion of the two gellants in the water-immiscible phase, this is often from 8 to 22% w/w of the phase and in many desirable embodiments from 10 to 17% w/w.

When structurants (iic), (iid) and (iie) are employed in conjunction with either of structurants (iia) or (iib), the weight ratio of (iic), (iid) or (iie) to structurant (i) is conveniently selected in the range of from 1:1 to 1:10, and in a number of acceptable embodiments from 40:60 to 1:7. When structurant (iic), (iid) and (iie) are employed in conjunction with either of structurants (iia) or (iib), the weight of structurant (iic) (iid) or (iie) can conveniently be from 0.25 to 2% of the composition, and in various desirable instances from 0.5 to 1.5% w/w.

Continuous Phase—Carrier Oils

The water-immiscible carrier liquid for the contiuous phase comprises one or a mixture of materials which are relatively hydrophobic so as to be immiscible in water. Following partition between the continuous phase and the disperse phase, a small fraction of hydrophilic liquid may remain in the continuous phase, provided the overall carrier liquid mixture is immiscible with water. It will generally be desired that the carrier oils mixture is liquid (in the absence of structurant) at temperatures of 15° C. and above. It may have some volatility but its vapour pressure will generally be less than 4 kPa (30 mmHg) at 25° C. so that the material can be referred to as an oil or mixture of oils. More specifically, it is desirable that at least 80% by weight of the hydrophobic carrier liquid should consist of materials with a vapour pressure not over this value of 4 kPa at 25° C.

It is preferred that the hydrophobic carrier material includes a volatile liquid silicone, i.e. liquid polyorganosiloxane. To class as "volatile" such material should have a measurable vapour pressure at 20 or 25° C. Typically the vapour pressure of a volatile silicone lies in a range from 1 or 10 Pa to 2 kPa at 25° C.

It is desirable to include volatile silicone because it gives a "drier" feel to the applied film after the composition is applied to skin.

Volatile polyorganosiloxanes can be linear or cyclic or mixtures thereof. Preferred cyclic siloxanes include polydimethylsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $10^{-5}$ m$^2$/sec (10 centistokes), and particularly above $10^{-7}$ m$^2$/sec (0.1 centistokes), the linear siloxanes normally exhibiting a viscosity of below $5 \times 10^{-6}$ m$^2$/sec (5 centistokes). The volatile silicones can also comprise branched linear or cyclic siloxanes such as the aforementioned linear or cyclic siloxanes substituted by one or more pendant —O—Si(CH$_3$)$_3$ groups. Examples of commercially available silicone oils include oils having grade designations 344, 345, 244, 245 and 246 from Dow Corning Corporation; Silicone 7207 and Silicone 7158 from Union Carbide Corporation; and SF1202 from General Electric.

The hydrophobic carrier employed in compositions herein can alternatively or additionally comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include products available under the trademarks Dow Corning 556 and Dow Corning 200 series. Other non volatile silicone oils include that bearing the trademark DC704. Incorporation of at least some non-volatile silicone oil having a high refractive index such as of above 1.5, eg at least 10% by weight (preferably at least 25% to 100% and particularly from 40 to 80%) of the silicone oils is often beneficial in some compositions, because this renders it easier to match the refractive index of the constituents of the composition and thereby easier to produce transparent or translucent formulations.

The water-immiscible liquid carrier may contain from 0% to 100% by weight of one or more liquid silicones. Preferably, there is sufficient liquid silicone to provide at least 1.0%, better at least 15%, by weight of the whole composition.

Silicon-free hydrophobic liquids can be used instead of, or more preferably in addition to liquid silicones. Silicon-free hydrophobic organic liquids which can be incorporated include liquid aliphatic hydrocarbons such as mineral oils or hydrogenated polyisobutene, often selected to exhibit a low viscosity. Further examples of liquid hydrocarbons are polydecene and paraffins and isoparaffins of at least 10 carbon atoms.

Other suitable hydrophobic carriers comprise liquid aliphatic or aromatic esters. Suitable aliphatic esters contain at least one long chain alkyl group, such as esters derived from $C_1$ to $C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they each have a melting point of below 20° C. These esters include isopropyl myristate, lauryl myristate, isopropyl palmitate, diisopropyl sebacate and diisopropyl adipate.

Suitable liquid aromatic esters, preferably having a melting point of below 20° C., include fatty alkyl benzoates.

Examples of such esters include suitable $C_8$ to $C_{18}$ alkyl benzoates or mixtures thereof, including in particular $C_{12}$ to $C_{15}$ alkyl benzoates eg those available under the trademark Finsolv. An aryl benzoate, such as benzyl benzoate can also be used. Incorporation of such alkyl or aryl benzoate esters as at least a fraction of the hydrophobic carrier liquid can be advantageous.

Further instances of suitable hydrophobic carriers comprise liquid aliphatic ethers derived from at least one fatty alcohol, such as myristyl ether derivatives e.g. PPG-3 myristyl ether or lower alkyl ethers of polygylcols such as an ether having named as PPG-14 butyl ether by the CTFA.

Aliphatic alcohols which are liquid at 20° C. may be employed herein, and it is especially desirable to employ those which are water-immiscible, and particularly those having a boiling point of higher than 100° C. These include branched chain alcohols of at least 10 carbon atoms and in many instances up to 30 carbon atoms, particularly 15 to 25, such as isostearyl alcohol, hexyl-decanol and octyl-dodecanol. Other suitable water-immiscible alcohols include intermediate chain length linear alcohols, commonly containing from 9 to 13 carbon atoms, such as decanol or dodecanol. A further suitable alcohol is benzyl alcohol. Such alcohols can assist in the process of forming a solution of the amido-substituted gellants (i) and/or (iia) to (iie) in a water-immiscible carrier liquid during the manufacture of structured gels. Such alcohols can often constitute from at least 10% or 15% by weight of the water-immiscible liquid carrier mixture, in many desirable mixtures comprising up to 70% or 80% of the mixture. In a number of convenient formulations, the proportion of such aliphatic alcohols in said mixture is from 10 or 15% to 30% by weight and in some others, the proportion is greater than 30% by weight.

However, aliphatic alcohols which are solid at 20° C., normally linear alcohols, such as stearyl alcohol are preferably absent or present in no more than 3% by weight of the whole composition, as indicated hereinbefore, since they lead to visible white deposits when a composition is topically applied to skin.

Silicon-free liquids can constitute from 0-100% of the water-immiscible liquid carrier, but it is preferred that silicone oil is present and that the amount of silicon-free constituents preferably constitutes up to 50 or 60% or even up to 80% of water-immiscible carrier liquid and in many instances from 10 to 60% by weight, eg 15 to 30% or 30 to 60% by weight, of the carrier liquid.

Liquid Disperse Phase

The emulsions herein contain a more polar or lypophobic disperse phase. The disperse phase may be a solution of an active ingredient, such as an active cosmetic ingredient.

The hydrophilic disperse phase in emulsions herein commonly comprises water as a solvent and can comprise one or more water soluble or water miscible liquids in addition to or in replacement of water. The proportion of water in an emulsion according to the present invention is often selected in the range of up to 60%, and particularly from 10% up to 40% or 50% of the whole formulation.

One class of water soluble or water-miscible liquids comprises short chain monohydric alcohols, e.g. $C_1$ to $C_4$ and especially ethanol or isopropanol, which can impart a deodorising capability to the formulation. Ethanol gives a cooling effect on application to skin, because it is very volatile. It is preferred that the content of ethanol or any other monohydric alcohol with a vapour pressure above 1.3 kPa (10 mmHg) is not over 15% better not over 8% by weight of the composition.

A further class of hydrophilic liquids comprises diols or polyols preferably having a melting point of below 40☐ C., or which are water miscible. Examples of water-soluble or water-miscible liquids with at least one free hydroxy group include ethylene glycol, 1,2-propylene glycol, 1,3-butylene glycol, hexylene glycols, such as, particularly, 1,2-hexane diol, diethylene glycol, dipropylene glycol, 2-ethoxyethanol, diethylene glycol monomethylether, triethyleneglycol monomethylether and sorbitol. Especially preferred are propylene glycol and glycerol.

The aqueous phase of the emulsion can additionally comprise an amino acid such as glycine or histidine, for example in a concentration of up to 10% by weight of the composition, such as from 3 to 8% by weight.

In emulsions herein the disperse phase normally constitutes from 5 to 80 or 85% of the weight of the composition preferably from 5 to 50 or 65% and more preferably from 25 or 35% up to 50 or 65%, while the emulsifier and the continuous phase with the structurant system and any water-immiscible cosmetic actives therein provides the balance. The weight proportion of continuous phase including the structurant normally constitutes from 15 or 35% up to 95% of the weight of the composition. Compositions with high proportion of disperse phase, i.e. from 65 to 85% disperse phase, may be advantageous because they can give good hardness even though the concentration of structurant may be only a small percentage of the total composition. However, compositions with a lower proportion of disperse phase can also be advantageous because they tend to offer a drier and warmer feel.

The emulsion compositions herein will generally include one or more emulsifying surfactants which may be anionic, cationic, zwitterionic and/or nonionic surfactants. The proportion of emulsifier in the composition is often selected in the range up to 10% by weight and in many instances from 0.1 or 0.25 up to 5% by weight of the composition. Most preferred is an amount from 0.1 or 0.25 up to 3% by weight. Nonionic emulsifiers are frequently classified by HLB value. It is desirable to use an emulsifier or a mixture of emulsifiers with an overall HLB value in a range from 2 to 10 preferably from 3 to 8.

It may be convenient to use a combination of two or more emulsifiers which have different HLB values above and below the desired value. By employing the two emulsifiers together in appropriate ratio, it is readily feasible to attain a weighted average HLB value that promotes the formation of an emulsion.

Many suitable emulsifiers of high HLB are nonionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditol as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. The hydrophobic moiety can be either linear or branched and is often saturated, though it can be unsaturated, and is optionally fluorinated. The hydrophobic moiety can comprise a mixture of chain lengths, for example those deriving from tallow, lard, palm oil, sunflower seed oil or soya bean oil. Such nonionic surfactants can also be derived from a polyhydroxy compound such as glycerol or sorbitol or other alditols. Examples of emulsifiers include ceteareth-10 to -25, ceteth-10-25, steareth-10-25 (i.e. $C_{16}$ to $C_{18}$ alcohols ethoxylated with 10 to 25 ethylene oxide residues) and PEG-15-25 stearate or distearate. Other suitable examples include $C_{10}$-$C_{20}$ fatty acid mono, di or tri-glycerides. Further examples include $C_{18}$-$C_{22}$ fatty alcohol ethers of polyethylene oxides (8 to 12 EO).

Examples of emulsifiers, which typically have a low HLB value, often a value from 2 to 6 are fatty acid mono or possibly diesters of polyhydric alcohols such as glycerol, sorbitol, erythritol or trimethylolpropane. The fatty acyl moiety is often from $C_{14}$ to $C_{22}$ and is saturated in many instances, including cetyl, stearyl, arachidyl and behenyl. Examples include monoglycerides of palmitic or stearic acid, sorbitol mono or diesters of myristic, palmitic or stearic acid, and trimethylolpropane monoesters of stearic acid.

A particularly desirable class of emulsifiers comprises dimethicone copolymers, namely polyoxyalkylene modified dimethylpolysiloxanes. The polyoxyalkylene group is often a polyoxyethylene (POE) or polyoxypropylene (POP) or a copolymer of POE and POP. The copolymers often terminate in $C_1$ to $C_{12}$ alkyl groups.

Suitable emulsifiers and co-emulsifiers are widely available under many trade names and designations including Abil™, Arlace™, Brij™, Cremophor™, Dehydrol™, Dehymuls™, Emerest™, Lameform™, Pluronic™, Prisorine™, Quest PGPH™, Span™, Tween™, SF1228™, DC3225™C and Q2-5200™.

Cosmetic Actives

The cosmetic actives employable herein can comprise antiperspirant or deodorant actives or pigments. Other cosemetic actives have sometimes previously been referred to as benefit agents. Such agents can include anti-dandruff agents, antiperspirants or deodorants, cosmetic abrasives, cosmetic astringents, depilating agents, epilatimng agents, hair conditioning agents, hair fixatives, hair colorants, hair waving or straightening agents, humectants, nail conditioning agents, skin conditioning agents or protectants, or sunscreen agents.

The present invention is particularly suitable for the incorporation of at least one water-soluble cosmetic active, for example from the foregoing list of actives, such as water-soluble antiperspirants or deodorants.

Antiperspirant Actives

The composition preferably contains an antiperspirant active. Antiperspirant actives, are preferably incorporated in an amount of from 0.5-60%, particularly from 5 to 30% or 40% and especially from 5 or 10% to 30 or 35% of the weight of the composition.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates and activated aluminium chlorohydrates.

Aluminium halohydrates are usually defined by the general formula $Al_2(OH)_xQ_y.wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever N V et al), the contents of which specification is incorporated herein by reference. Some activated salts do not retain their enhanced activity in the presence of water but are useful in substantially anhydrous formulations, i.e. formulations which do not contain a distinct aqueous phase.

Zirconium actives can usually be represented by the empirical general formula: $ZrO(OH)_{2n-nz}B_z.wH_2O$ in which z is a variable in the range of from 0.9 to 2.0 so that the value 2n−nz is zero or positive, n is the valency of B, and B is selected from the group consisting of chloride, other halide, sulphamate, sulphate and mixtures thereof. Possible hydration to a variable extent is represented by $wH_2O$. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have co-ordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_2(NH_2)COOH$.

It is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis.

Other actives which may be utilised include astringent titanium salts, for example those described in GB 2299506A.

When the active antiperspirant salt is incorporated in solution in a hydrophilic solvent such as a glycol, its weight commonly excludes any water of hydration present.

The antiperspirant active will often provide from 3 to 60% by weight of the disperse phase, particularly from 10% or 20% up to 55% or 60% of that phase.

Deodorant Actives

Suitable deodorant actives can comprise deodorant effective concentrations of antiperspirant metal salts, deoperfumes, and/or microbicides, including particularly bactericides, such as chlorinated aromatics, including biguanide derivatives, of which materials known as Igasan DP300™ (triclosan), Tricloban™, and Chlorhexidine warrant specific mention. A yet another class comprises biguanide salts such as are available under the trade mark Cosmocil™. Deodorant actives are commonly employed at a concentration of from 0.1 to 25% by weight.

Optional Ingredients

Optional ingredients include wash-off agents, often present in an amount of up to 10% w/w to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol.

A further optional constituent of the formulation comprises one or more further structurants which can be employed in addition to the combination of amido substituted gellant (i) and (iia) to (iie). Herein, said combination may be the primary structurant, by which is meant that is employed at a concentration that is higher than that of the further structurant.

The further structurants employable herein can be non-polymeric or polymeric. Solid linear fatty alcohol and/or a wax may be included but are not preferred. Such further structurants exclude fatty acids or salts thereof, such as stearic acid or sodium stearate or 12-hydroxy stearic acid, because they can form insoluble precipitates with aluminium ions. Suitable gellants can comprise dibenzylidene alditols, e.g. dibenzylidene sorbitol, that can be employed desirably in a proportion of in the range of from 0.1 to 0.5% by weight of the formulation.

Polymeric structurants which can be employed can comprise organo polysiloxane elastomers such as reaction products of a vinyl terminated polysiloxane and a cross linking agent or alkyl or alkyl polyoxyalkylene-terminated poly (methyl substituted) or poly (phenyl substituted) siloxanes. A number of polyamides have also been disclosed as structurants for hydrophobic liquids. Polymers containing both siloxane and hydrogen bonding groups, which might be used as secondary structurants, have been disclosed in WO 97/36572 and WO 99/06473. Polyacrylamides, polyacrylates or polyalkylene oxides may be used to structure or thicken the disperse phase.

The compositions herein can incorporate one or more cosmetic adjuncts conventionally contemplatable for cosmetic solids or soft solids. Such cosmetic adjuncts can include skin feel improvers, such as talc or finely divided polyethylene, for example in an amount of up to about 10%; skin benefit agents such as allantoin or lipids, for example in an amount of up to 5%; colours; skin cooling agents other than the already mentioned alcohols, such a menthol and menthol derivatives, often in an amount of up to 2%, all of these percentages being by weight of the composition. A commonly employed adjunct is a perfume, which is normally present at a concentration of from 0 to 4% and in many formulations from 0.25 to 2% by weight of the composition.

Emulsion sticks made with the combination of gellants, (i) and one or more of (iia) to (iie), are non-whitening and have a good skin feel. They can also be made with sufficient translucency to be perceived as clear.

Composition Preparation

A convenient process sequence for preparing a composition according to the present invention comprises first forming a solution of the structurant combination in the water-immiscible liquid or one of the water-immiscible liquids. This is normally carried out by agitating the mixture at a temperature sufficiently high that all the structurants dissolve (the dissolution temperature) such as a temperature in a range from 70 to 140° C. Any oil-soluble cosmetic active can be introduced into oil phase, either before or after the introduction of the structurants. Commonly the resultant structurant solution is allowed to cool to a temperature that is intermediate between that at which the structurants dissolved and the temperature at which it would set, often reaching a temperature in the region of 60 to 90° C.

In some convenient preparative routes, it is desirable to dissolve all or a fraction of the amide-substituted structurants in a liquid component of the composition, such as an alcohol, eg an alcoholic carrier fluid, ie, a branched aliphatic alcohol, eg isostearyl alcohol or octyldodecanol, optionally in conjunction with an alcohol having some water-miscibility and boiling point above the dissolution temperature of DOPAD in the alcoholic fluid. This enables the remainder of the carrier fluids to avoid being heated to the temperature at which the structurants dissolve or melt. The proportion of the carrier fluids for dissolving the structurants is often from 15 to 65% by weight of the carrier fluids, and particularly from 20 to 40%. Separately, an aqueous or hydrophilic phase is prepared by introduction of a water-soluble cosmetic active, such as an antiperspirant active, into the liquid part of that phase (if this is necessary: antiperspirant actives can sometime be supplied in aqueous solution which can be utilised as is).

Any emulsifier can be mixed into either the water-immiscible or the hydrophylic phase before they are mixed.

If possible, this solution of cosmetic active which will become the disperse phase is preferably heated to a temperature similar to that of the continuous phase with structurant therein when the two materials are mixed together, but without exceeding the boiling point of the hydrophylic solution, and then mixed with the continuous phase. Alternatively, the solution is introduced at a rate which maintains the temperature of the mixture. If it is necessary to work at a temperature above the standard boiling temperature of the disperse phase, or at a temperature where evaporation from this phase is significant, a pressurised apparatus could be used to allow a higher temperature to be reached. With the structurant materials of this invention for the continuous phase, this is usually unnecessary. After the two phases are mixed, the resulting mixture is filled into dispensing containers, typically at a temperature 5 to 30° C. above the regular setting temperature of the composition, and cooled or allowed to cool to ambient temperature. Cooling may be brought about by nothing more than allowing the container and contents to cool. Cooling may be assisted by blowing ambient or even refrigerated air over the containers and their contents.

Product Dispenser

Emulsion sticks according to the present invention are normally housed in dispensing containers, the shape and size of which, the materials of their construction and the mechanisms employed therein for dispensing the sticks are those commensurate with the cosmetic. Thus, by way of example, an antiperspirant or deodorant stick is often housed in a barrel, commonly of circular or elliptical transverse cross section, having an open end through which the stick can pass and an opposed closed end, commonly comprising a platform or elevator that is axially moveable along the barrel. The platform can be raised by the insertion of a finger or more commonly by rotation of an externally exposed rotor wheel that rotates a threaded spindle extending axially through a cooperating threaded bore in the platform. The barrel normally also has a removable cap that can fit over its open end. The barrel is normally made from an extrudable thermoplastic such as polypropylene or polyethylene.

The present invention also provides cosmetic products comprising an invention cosmetic stick as described hereinbebefore disposed within a dispensing barrel.

Having summarised compositions according to the present invention and described preferred embodiments, specific embodiments thereof will now be described in more detail by way of example only.

The following constituents were employed in exemplified and comparison emulsion sticks hereinafter.

| Ref | CTFA or IUPAC name | Trade name and/or supplier |
|---|---|---|
| C1 | Cyclomethicone | DC245, Dow Corning |
| C2 | C$_{12-14}$ alkyl benzoate | Finsolv TN, Finetex |
| C3 | Isostearyl alcohol | Prisorine 3515, Uniqema |
| C4 | 2-hexyl-decanol | Eutanol G16, Cognis |
| C5 | Benzyl benzoate | Pentagon Chemicals Ltd |
| C6 | 1,1,5,5 tetraphenyl,-1,3,3,5-tetramethyl trisiloxane | DC704, Dow Corning |
| C7 | octyl dodecanol | Eutanol G, Cognis |
| C8 | C12-C16 branched fatty alcohols | Isofol 14T, Sasol |
| G1 | N-(2-ethyl hexanoyl)-L-glutamic acid di-n-butylamide | GA-01, Ajinomoto |
| G2 | N-lauroyl-L-glutamic acid di-n-butylamide | GP-1, Ajinomoto |
| G3 | (5-benzyl-3,6-dioxo-2-piperazin-2-yl)-acetic acid, 2-isopropyl-5-methyl-phenyl ester | preparation as per Ex 1.2 of PCT/EP 02/14525 (published as WO 03/059307) |
| G4 | N N'-bis (dodecanoyl)-1,2-diaminocyclohexane (non optically active cis/trans mixture) . . . | Preparation as in U.S. Pat. No. 6410003 |
| G5 | N N'-bis (2-ethylhexanoyl)-1,2-diaminocyclohexane (non optically active cis/trans mixture) . . . | Preparation as per U.S. Pat. No. 6410003 |
| G6 | 2-octadecyl-N,N'-dibutylsuccinamide (P&G dicarboxylic acid amide) | Preparation as per U.S. Pat. No. 6190673 |
| G7 | n-propyl-12-hydroxystearamide | |
| G8 | 2-hydroxy-1,2,3-propane trioctylamide (P&G tricarboxylic acid amide) | Preparation as per U.S. Pat. No. 6190673 |
| G9 | 2-methyl pentanoyl-L-glutamic acid di-n-butylamide | In-house preparation |
| G10 | isopentanoyl-L-glutamic acid di-n-butylamide | In-house preparation |
| D1 | Water | demineralised, in-house |
| D2 | Glycerol | Prisorine 3515, Uniqema |
| D3 | Al/Zr pentachlorohydrate 50% aqueous solution | Zirconal 50, BK Giulini |
| D4 | Al/Zr Tetrachlorohydrex glycine complex | Reach 908, Rehies |
| D5 | Al/Zr Tetrachlorohydrex glycine complex | Rezal 36 GP, Rehies |
| D6 | Propylene Glycol | Fisher |
| D7 | Glycine: | Fisher |
| E1 | Dimethicone Copolyol | Abil EM90, Th. Goldschmidt |
| E2 | PPG-30 Dipolyhydroxystearate | Arlacel P135, Uniqema |
| F | Fragrance | |
| S1 | hydrophobic fumed silica | HDK H30, Wacker |

When measured in any of the Examples and Comparisons, payoff of the stick was measured on black cotton, and visible deposits (whiteness) were measured on black cotton 24 hours after application of the stick.

EXAMPLE 1.1 AND COMPARISON 1.A

These Example and comparison sticks were made by the following general method M1:—

An antiperspirant salt solution was first prepared either by combining antiperspirant salt solution D3 with the glycerol D2, or by dissolving the antiperspirant powder D4 in water D1 at laboratory ambient temperature (circa 22° C.).

The gellants, G1, G2 or G3 or combinations, were dissolved in the fatty alcohol carrier oil (C2 or C3) whilst being stirred using an overhead paddle stirrer (temperature reaching typically 120-140° C.). Any remaining water immiscible carrier oils (C1, C2, C5) and the emulsifier E1 were combined with each other at room temperature. This carrier oil mixture was sheared at 2500 rpm with a Silverson™ mixer and the antiperspirant salt solution slowly added. The shear rate was then increased to 7500 rpm for 5 minutes. The resulting emulsion was then heated to 85° C. in an oil bath. The gellant solution was allowed to cool to 85-90° C. and the emulsion was added to this. The mixture was stirred under low shear (paddle stirring) to achieve complete mixing. Where employed, fragrance was also added at this stage. The resultant mixture was allowed to cool and then poured into stick barrels at the temperature indicated below, which was in the region of 5° C. above its regular solidification temperature (obtained by allowing a sample to solidify under quiescent conditions, or from previous trials), and allowed to cool to ambient.

The formulations expressed in parts by weight and the properties of the sticks are summarised in Table 1 below:

TABLE 1

| | Ex 1.1 | Co 1.A |
|---|---|---|
| | % by weight | |
| Constituent | | |
| G1 | 3.0 | |
| G2 | 3.0 | 6 |
| C4 | 17.5 | 17.5 |
| C1 | 35 | 35 |
| D4 | 23.61 | 24.04 |
| D1 | 16.39 | 15.96 |
| E1 | 0.5 | 0.5 |
| F1 | 1.0 | 1.0 |
| Process Conditions | | |
| Pour Temp (° C.) | 70 | 65 |
| Stick properties | | |
| Hardness (mm) | 13.7 | 18.7 |
| pay-off (g) | 0.60 | 0.70 |

Ex 1.1 was a firm slightly translucent stick. It dried quickly on skin without leaving any white or oil/greasy deposit.

Comparative Co 1.A was a rather soft, white opaque stick, that left a thick greasy film when applied to skin

EXAMPLES 2.1 TO 2.7 AND COMPARISONS CO 2.A TO CO 2.D

These Example and Comparison sticks procedure were made by a second general process M2 which was the same as process M1 above, except as follows:

The proportions of components in the continuous and disperse phase of the stick were initially determined (through calculation and measurement) such that the two phases had quite closely matched refractive indices (RIs) at 25° C. The RIs of the separate phases containing the determined proportions of constituents were measured at ambient temperature (25° C.) prior to being mixed together and the RI of the external phase oil phase was adjusted by adding enough of one of the oils such that it closely matched that of the internal phase.

The proportions expressed in parts by weight of the formulations and the stick properties are summarised in Table 2 below.

TABLE 2

| Constituent | Ex 2.1 | Co 2.A | Ex 2.2 | Co 2.B | Ex 2.3 | Co 2.C |
|---|---|---|---|---|---|---|
| | | | % by weight | | | |
| G1 | 2 | 5 | 4 | | 2 | 3 |
| G2 | 3 | | 4 | 8 | | |
| G3 | | | | | 1 | |
| D2 | 19.6 | 19.6 | 18.27 | 18.27 | 20.48 | 20.55 |
| C2 | 5.3 | 5.3 | 4.96 | 4.96 | 5.54 | 5.54 |
| C1 | 15.6 | 19.6 | 18.27 | 18.27 | 20.48 | 20.41 |
| D3 | 40 | 40 | 40 | 40 | 40 | 40 |
| D2 | 10 | 10 | 10 | 10 | 10 | 10 |
| E1 | 0.5 | 0.5 | 0.5 | 0.5 | 0.5 | 0.5 |
| Process Conditions | | | | | | |
| Pour Temp (° C.) | 70 | Dnp | 80 | 80 | 70 | 75 |
| Stick Properties | | | | | | |
| Hardness (mm) | 15.2 | | 9.6 | 13.9 | 13.5 | 17.4 |
| pay-off (g) | 0.67 | | 0.46 | 0.50 | n/d | 0.79 |
| % Transmission | 0.85 | | 0.80 | 0.10 | 0.60 | 0.10 |

| Constituents | Ex 2.4 | Ex 2.5 | Co 2.D | Ex 2.6 | Ex 2.7 |
|---|---|---|---|---|---|
| | | | % by weight | | |
| G1 | 3.25 | 3.75 | | 2 | 3 |
| G2 | 3.25 | 3.75 | 7.5 | | |
| G3) | | | | 1 | 1.2 |
| C4 | 25 | 24.52 | 24.52 | 28.5 | 28.5 |
| C2 | 11.5 | 11.28 | 11.28 | 11.5 | 11.5 |
| C5 | 1.0 | 0.98 | 0.98 | 1.0 | 1.0 |
| C1 | 14.5 | 14.22 | 14.22 | 14.5 | 14.5 |
| D4 | 23.61 | 23.61 | 23.61 | 23.61 | 23.92 |
| D1 | 16.39 | 16.39 | 16.39 | 16.39 | 15.88 |
| E1 | 0.5 | 0.5 | 0.5 | 0.5 | 0.5 |
| F1 | 1.0 | 1.0 | 1.0 | 1.0 | |
| Process Conditions | | | | | |
| Pour Temp (° C.) | 70 | 70 | 70 | 65 | 65 |
| Stick Properties | | | | | |
| Hardness (mm) | 14.3 | 13.1 | 18.2 | 17.1 | 15.0 |
| pay-off (g) | 0.56 | 0.51 | 0.71 | 0.79 | 0.60 |
| whiteness | | 20.4 | | | 17.7 |
| % Transmission | 1.6 | 1.7 | 0.22 | 0.90 | 0.78 |

The pour temperature of the full emulsion in Co 2.A could not be measured because the gellant solution gelled at 110° C. which is higher than that at which the rest of the emulsion could be added.

Ex 2.1 was a reasonably firm, translucent stick. It applied well to skin leaving no white deposit. It did initially leave a slight oily film, but this rapidly disappeared. Ex 2.2 was a very firm translucent slick. It applied well to skin and left no white deposit or oily/greasy film.

Comp Co 2.B was a reasonably firm opaque stick, but when applied to skin it left a thick oily film, but no visible white deposit.

Ex 2.3 was a reasonably firm, slightly translucent sick. It applied well to skin leaving no oily/greasy film and no visible white deposit Comp Co 2.C was a rather soft opaque stick which left a thick greasy film when applied to skin.

Formulations Ex 2.2 and Co 2.B were stored at 25 and 45° C. for 3 weeks. Both samples of Ex 2.2 remained very firm. The sample of Co 2.B when stored at 45° C., however, was significantly softer than that stored at 25° C.

Ex 2.4 was a reasonably firm translucent stick. It applied well to skin leaving no white deposit and no oily/greasy film.

Ex 2.5 was a firm translucent stick. It applied well to skin leaving no white deposit and no oily/greasy film.

Comp Co 2.D was a reasonably firm, slightly translucent stick when freshly made. However, after 18 hrs at room temperature it had become a rather soft opaque stick. It left a thick waxy film when applied to skin.

Ex 2.6 was a slightly soft translucent stick. It, however, applied well to skin leaving no white deposits and no oily/greasy film.

Ex 2.7 was a firm translucent stick. It applied well to skin leaving no white deposit and no oily/greasy film.

Further compositions according to the present invention can be made by substituting the same amount of cis/trans-1,2-di-dodecanamidocyclohexane, or 1,3,5-tri (dodecylaminocarbonyl)cyclohexane or 2-dodecyl-N,N'-dibutylsuccinamide or N-propyl-12-hydroxystearamide for Ajinimoto gellant GP-1 (G2) in any one of Examples 1.1, or 2.1 to 2.7.

EXAMPLES 3.1 TO 3.4

The compositions in Examples 3.1 to 3.4 were made by the general process M1, employing the parts by weight of constituents as shown in Table 3 below, employing an additional amide gellant. The stick properties are summarised in Table 3.

TABLE 3

| | Ex 3.1 | Ex 3.2 | Ex 3.3 | Ex 3.4 | Ex 3.5 |
|---|---|---|---|---|---|
| G1 | 3.0 | 3.0 | 3.0 | 3.0 | 3.5 |
| G2 | 3.0 | 3.0 | 3.0 | 3.0 | 3.5 |
| G4 | | 1.5 | | | |
| G5 | 1.5 | | | | |
| G6 | | | 1.5 | | |
| G7 | | | | 1.5 | |
| G8 | | | | | 0.5 |
| C4 | 24.52 | 24.52 | 24.52 | 24.52 | 24.52 |
| C2 | 11.28 | 11.28 | 11.28 | 11.28 | 11.28 |
| C5 | 0.98 | 0.98 | 0.98 | 0.98 | 0.98 |
| C1 | 14.22 | 14.22 | 14.22 | 14.22 | 14.22 |
| D5 | 23.96 | 23.96 | 23.96 | 23.96 | 23.96 |
| D1 | 16.04 | 16.04 | 16.04 | 16.04 | 16.04 |
| E1 | 0.5 | 0.5 | 0.5 | 0.5 | 0.5 |
| F | 1.0 | 1.0 | 1.0 | 1.0 | 1.0 |
| Stick Pour Temp (° C.) | 70 | 70 | 65 | 65 | 65 |
| Properties | | | | | |
| Hardness (mm) | 13.6 | 15.9 | 16.2 | 14.6 | 15.4 |
| pay-off (black cotton) (g) | 0.482 | 0.419 | 0.499 | 0.434 | 0.457 |
| % Transmission | 5.32 | 2.3 | 3.0 | 2.2 | 1.9 |

EXAMPLES 4.1 TO 4.15

Further refractive index matched emulsions were made employing a combination of gellant (i) and (iia) and the remaining constituents summarised in Table 4 below. Examples 4.1-4.3 and 4.10 to 4.15 were made in accordance with general method M1, Gland G2 being combined with carrier C4 initially, Example 4.4 to 4.8 were made by method M3 below and Example 4.9 by method M4 below. These Examples varied the level and type of emulsifier, the selection of carriers including carriers with a longer aliphatic backbone and their concentrations, the presence of an inorganic particulate, the presence of a dihydric alcohol and glycine.

Method M3

In a first step, the gellants, emulsifier, oils and silica (where present) were heated in a beaker on a hot plate, until complete dissolution of the gellants had occurred, reaching a maximum temperature not exceeding 135° C. The contents of the beaker were stirred using a Silverson™ mixer, at about 3000 rpm. This oil phase solution was then allowed to cool to 95° C.

In a second step, which was carried out at the same time as the first step, the solution of antiperspirant active solution (aqueous phase) was heated in a second beaker in an oil bath (at 90° C.) until it attained 70° C.

In a third step, the hot aqueous phase of step 2 was added slowly into the oil phase of step 1, ensuring that the temperature did not drop below 85° C. The mixer speed was increased gradually during aqueous phase addition to 8000 rpm and shearing at that speed continued for a further 3 minutes. The fragrance was then introduced, the temperature being from 82 to 85° C.

In the final step, the fragranced mixture was allowed to cool to a temperature in the region of 5° C. above its solidification temperature and poured into stick barrels at the temperature indicated in Table 5.

Method M4

In the first step, a first oil phase was prepared by shear mixing oils C1 and C3 and the emulsifier at 3000 rpm, at laboratory ambient temperature.

The second step was the same as in method M3.

In the third step a second oil phase was prepared by dissolving the gellants in oil C4 similarly to step 1 of M3 but using a magnetic flea to stir and then allowed to cool to about 100° C.

In the fourth step, the aqueous phase of step 2 was added slowly to oil phase I with gradual increase in stirrer speed during addition to 8000 rpm. The resulting emulsion was then heated to 80° C. on a hot plate and fragrance added.

In the fifth step, the cooled second oil phase was gently stirred into emulsion of the fourth step, with the aid of a glass thermometer.

Finally the sample was poured into stick barrels at 78° C., which is significantly above its solidification temperature. The formulation ingredients expressed in parts by weight and the stick properties are summarised in Table 4 below.

TABLE 4

|   | Ex 4.1 | Ex 4.2 | Ex 4.3 | Ex 4.4 | Ex 4.5 |
|---|---|---|---|---|---|
| G1 | 4 | 4 | 4 | 4 | 4 |
| G2 | 4 | 4 | 4 | 4 | 4 |
| C1 | 16.13 | 13.9 | 18.62 | 13.75 | 22.44 |
| C2 | 11.59 | 11.28 |  | 11.55 |  |
| C4 | 22.17 | 25.42 | 25.3 | 25.3 | 22.58 |
| C5 | 1.01 |  |  |  |  |
| C6 |  |  | 6.68 |  |  |
| D1 | 16.04 | 16.04 | 16.04 | 16.0 | 21.58 |
| D5 | 23.96 | 23.96 | 23.96 | 24.0 | 24.0 |
| E1 | 0.1 | 0.4 | 0.4 | 0.4 | 0.4 |
| F | 1.0 | 1.0 | 1.0 | 1.0 | 1.0 |
| Properties |  |  |  |  |  |
| Stick Pour Temp (° C.) | 80 | 80 | 80 | 78 | 78 |
| Hardness (mm) | 14.6 | 13.0 | 13.8 | 12.8 | 12.3 |
| pay-off (black cotton) (g) | 0.476 | 0.474 | 0.424 | 0.461 | 0.42 |
| % Transmission | 2.0 | 7.9 | 4.8 | 23.9 | 4.0 |

TABLE 4-continued

|   | Ex 4.6 | Ex 4.7 | Ex 4.8 | Ex 4.9 | Ex 4.10 | Ex 4.11 |
|---|---|---|---|---|---|---|
| G1 | 4 | 4 | 4 | 4 | 3.2 | 4.8 |
| G2 | 4 | 4 | 4 | 4 | 4.8 | 3.2 |
| C1 | 5.61 | 16.13 | 13.61 | 13.70 | 13.48 | 13.48 |
| C3 |  | 9.0 | 11.4 | 11.0 | 9.14 | 9.14 |
| C4 | 44.9 |  | 25.26 | 25.3 | 22.98 | 22.98 |
| D1 | 16.0 | 16.0 | 16.0 | 16.0 | 16.0 | 16.0 |
| D2 |  | 25.47 |  |  |  |  |
| D5 | 24.0 | 24.0 | 24.0 | 24.0 | 24.0 | 24.0 |
| D6 |  |  |  |  | 5.0 | 5.0 |
| E1 | 0.4 | 0.4 | 0.4 |  | 0.4 | 0.4 |
| E2 |  |  |  | 1.0 |  |  |
| S1 |  |  | 0.33 |  |  |  |
| F | 1.0 | 1.0 | 1.0 | 1.0 | 1.0 | 1.0 |
| Properties |  |  |  |  |  |  |
| Stick Pour Temp (° C.) | 82 | 83 | 83 | 78 | 78 | 80 |
| Hardness (mm) | 14.6 | 12.1 | 12.5 | nm | 11.1 | 12.2 |
| pay-off (black cotton) (g) | 0.494 | 0.463 | 0.468 | nm | 0.484 | 0.458 |
| % Transmission | 60.3 | 58.4 | 8.2 | 0.73 | 8.3 | 32.6 |

|   | Ex 4.12 | Ex 4.13 | Ex 4.14 | Ex 4.15 |
|---|---|---|---|---|
| G1 | 4.0 | 4.0 | 3.5 | 4.0 |
| G2 | 4.0 | 4.0 | 3.5 | 4.0 |
| C7 | 27.38 | 27.38 | 23.96 |  |
| C8 |  |  |  | 25.3 |
| C2 | 19.81 | 19.85 | 23.08 | 12.49 |
| C1 | 6.37 | 6.42 | 7.33 | 12.81 |
| D5 | 19.0 | 19.0 | 19.0 | 24.0 |
| D7 | 5.59 | 5.59 | 5.59 |  |
| E1 | 0.2 | 0.1 | 0.4 | 0.4 |
| F | 1.0 | 1.0 | 1.0 | 1.0 |
| Properties |  |  |  |  |
| Stick Pour Temp (° C.) | 88 | 90 | 85 | 72 |
| Hardness (mm) | 10.2 | 10.7 | 10.9 | 11.7 |
| pay-off (black cotton) (g) | 0.41 | 0.49 | 0.41 | 0.463 |
| % Transmission | 6.6 | 5.6 | 5.1 | 17.7 | nm indicates in the Table that the measurement was not made.

EXAMPLES 5.1 AND 5.2

These Examples were made using further examples of class (i) gelators (G9 and G10) and the remaining constituents identified in Table 6 below, in parts by weight. They were made by method M1. The stick properties are summarised in Table 6.

Preparative Method for gellants G9 and G10

Gelants G9 and G10 were made by a two stage method. In stage 1 the N-acyl L glutamic acid dimethyl ester was formed and in stage 2, this was converted to the corresponding N-acyl L glutamic acid dibutlyamide, both stages employing laboratory grade chemicals from Sigma Aldrich.

A 250 ml 3 necked round bottomed flask equipped with a magnetic stirrer was charged with L-Glutamic acid dimethyl ester hydrochloride salt (15 g, 71 mmol). Dichloromethane (150 ml, approximately 10 mls per gram of the HCl salt) was then introduced to the flask at laboratory ambient temperature (20° C.) with stirring.

Triethylamine (TEA, 8.61 g, 85 mmol) was then added with stirring, whereupon a white precipitate immediately appeared. This mixture was left to stir at room temperature for a period of 60 minutes. A second portion of TEA (7.17 g, 71 mmol) was then added to the reaction mixture together with the respective acid chloride (71 mmol in 50 ml DCM) (2-ethyl-butanoic acid chloride for Ex5.1 and isopentanoic acid chloride for Ex 5.2) whilst maintaining the temperature between 0° C.-10° C. during the addition. The reaction mixture was stirred overnight at ambient temperature.

Next morning, the precipitate was filtered off and a clear filtrate was obtained which was washed successively with dilute hydrochloric acid, saturated sodium bicarbonate solution and water in a separating funnel. Evaporation of all solvent under reduced pressure yielded the corresponding N-Acyl L-Glutamic acid dimethyl ester which was detected to be free from residual acid and starting materials.

In the second stage, the product of stage 1 (typically 10 g, 23-38 mmol) was dissolved in toluene (100 ml, 10 mls per gram of dimethyl ester) then added to a 250 ml reactor vessel equipped with magnetic stirrer, dropping funnel and water condenser. Butylamine in excess (30-50 ml, 300-500 mmol) was then introduced slowly dropwise, after which the reaction solution was heated up to 90° C. and stirred thoroughly. Progress of the conversion from dimethyl ester to diamide was monitored using both RP HPLC and FT-IR on withdrawn samples until no ester was detected any longer or if some ester remained, until the relative intensity of the ester versus the amide infra-red peaks had become constant. The reaction took approximately 24 hours.

When cooled to ambient temperature, the reaction mixture formed a gel which was filtered under vacuum and washed with cold solvent until a crude white solid material was obtained. Residual butylamine was removed by washing the crude product with 25 g acid based Amberlyst A-15™ resin in ethanol, followed by filtration through charcoal or a further wash with base resin (Amberlyst A-21™, 25 g) was also carried out to remove any remaining impurities or filtration through charcoal to remove colour as per Table 5.

TABLE 5

| N-Acyl Derivative | Gellant | Purification Step | Purity (Area %) | M P (° C.) |
|---|---|---|---|---|
| 2-methyl pentanoyl | G9 | Acid resin/charcoal/ethanol | 94.06 | 172 |
| Isopentanoyl | G10 | Acid resin/base resin/ethanol | 98.02 | 194 |

TABLE 6

|  | Ex 5.1 | Ex 5.2 |
|---|---|---|
| G9 | 3.0 |  |
| G10 |  | 4.0 |
| G2 | 3.0 | 4.0 |
| C1 | 14.3 | 6.17 |
| C2 | 12.0 |  |
| C4 | 26.3 | 44.43 |
| D1 | 16.0 | 16.0 |
| D5 | 24.0 | 24.0 |
| E1 | 0.4 | 0.4 |
| F | 1.0 | 1.0 |
| Properties |  |  |
| Hardness (mm) | 19.0 | 13.2 |
| Pour Temp | 55 | 70 |
| Clarity (% Transmission) | 1.2 | 3.1 |

Both sticks were translucent in appearance. Ex 5.1 demonstrates that the combination of gellants G9 and G2 produces a stick that is not quite as firm as the combination of G1 and G2 at the same concentrations. When a firmer stick is desired, it can be attained by increasing the concentrations.

Measurement of Properties i) Stick Hardness—Penetrometer

The hardness and rigidity of a composition which is a firm solid can be determined by penetrometry. If the composition is a softer solid, this will be observed as a substantial lack of any resistance to the penetrometer probe.

A suitable procedure is to utilises a lab plant PNT penetrometer equipped with a Seta wax needle (weight 2.5 grams) which has a cone angle at the point of the needle specified to be 9°10' +/−15". A sample of the composition with a flat upper surface is used. The needle is lowered onto the surface of the composition and then a penetration hardness measurement is conducted by allowing the needle with its holder to drop under a total weight, (i.e. the combined weight of needle and holder) of 50 grams for a period of five seconds after which the depth of penetration is noted. Desirably the test is carried out at a number of points on each sample and the results are averaged. Utilising a test of this nature, an appropriate hardness for use in an open-ended dispensing container is a penetration of less than 30 mm in this test, for example in a range from 2 to 30 mm. Preferably the penetration is in a range from 5 mm to 20 mm.

In a specific protocol for this test measurements on a stick were performed in the stick barrel. The stick was wound up to project from the open end of the barrel, and then cut off to leave a flat, uniform surface. The needle was carefully lowered to the stick surface, and then a penetration hardness measurement was conducted. This process was carried out at six different points on the stick surface. The hardness reading quoted is the average value of the 6 measurements.

ii) Deposition by Firm Sticks (Pay-off)

A second property of a composition is the amount of it which is delivered onto a surface when the composition is drawn across that surface (representing the application of a stick product to human skin), sometimes called the pay-off. To carry out this test of deposition when the composition is a firm stick, able to sustain its own shape, a sample of the composition with standardised shape and size is fitted to apparatus which draws the sample across a test surface under standardised conditions of temperature and applied pressure a specified number of times (thrice each way). The amount transferred to the surface is determined as an increase in the weight of the substrate to which it is applied. If desired the colour, opacity or clarity of the deposit may subsequently be determined. A specific procedure for such tests of deposition and whiteness applicable to a firm solid stick used apparatus to apply a deposit from a stick onto a substrate under standardised conditions and then measures the mean level of white deposits using image analysis.

The substrates used were 12×28 cm strips of black cotton fabric. The substrates were weighed before use. The sticks were previously unused and with domed top surface unaltered.

The apparatus comprised a flat base to which a flat substrate was attached by a clip at each end. A pillar having a mounting to receive a standard size stick barrel was mounted on an arm that was moveable horizontally across the substrate by means of a pneumatic piston.

Each stick was kept at ambient laboratory temperature overnight before the measurement was made. The stick was advanced to project a measured amount from the barrel. The barrel was then placed in the apparatus and a spring was positioned to bias the stick against the substrate with a standardised force (500 g load). The apparatus was operated to pass the stick 120 mm laterally across the substrate six times with a final velocity of 140 mm/s. The substrate was carefully removed from the rig and reweighed. The whiteness of the deposit could subsequently be measured as described at (v) below.

(iii) Whiteness of Deposit

The deposits from the test (ii) above, were assessed for their whiteness after an interval of 24 hours approximately. This was carried out using a KS Image Analyser fitted with a Sony XC77 monochrome video camera with a Cosmicar 16 mm focal length lens positioned vertically above a black table illuminated from a high angle using fluorescent tubes to remove shadowing. The apparatus was initially calibrated using a reference white card, after the fluorescent tubes had been turned on for long enough to give a steady light output. A cloth with a deposit thereon from the previous test was placed on the table and the camera was used to capture an image. An area of the image of the deposit was selected and analysed using KS400™ image software. This notionally divided the image into a large array of pixels and measured the grey level of each pixel on a scale of 0 (black) to 255 (white). The average of the grey intensity was calculated and can be compared with the background reading for the cloth of 10. This was a starting point to measure the whiteness of the deposit, with higher numbers indicating a whiter deposit. It was assumed that low numbers show a clear deposit allowing the substrate colour to be seen.

(iv) Clarity of Formulation—Light Transmission

The translucency of a composition may be measured by placing a sample of standardised thickness in the light path of a spectrophotometer and measuring transmittance, as a percentage of light transmitted in the absence of the gel.

This test was carried out using a dual-beam Perkin Elmer Lambda 40 spectrophotometer. The sample of composition was poured hot into a 4.5 ml cuvette made of poly(methylmethacrylate) (PMMA) and allowed to cool to an ambient temperature of 20-25° C. Such a cuvette gives a 1 cm thickness of composition. Measurement was carried out at 580 nm, with an identical but empty cuvette in the reference beam of the spectrophotometer, after the sample in the cuvette had been held for 24 hours. A transmittance measured at any temperature in the range from 20-25° C. is usually adequately accurate, but measurement is made at 25° C. if more precision is required.

(v) HPLC Method for Purity of Gellant

Purity of the gellant was measured by reverse phase HPLC with UV detection.

A mobile phase was prepared comprising a 300 ml aliquot of deionised water, to which was added a 700 ml aliquot of HPLC grade acetonitrile and 11.0 ml of trifluoroacetic acid (Aldrich™ spectrophotometric grade), all solvents were then mixed thoroughly and degassed. 0.001 g of sample was weighed into a 2 ml HPLC vial and made up to volume with the mobile phase.

The sample was then analysed using a Hewlett Packard 1050 HPLC System™ equipped with a Hypersil ODS 5 µm $C_{18}$, 250×4.6 mm ID column, HP Autosampler™ and UV Diode Array Detector set to 210 nm.

Analysis was carried out under the following conditions:—

| Isocratic/gradient | Isocratic |
|---|---|
| Flow rate | 1.2 ml/minute |
| Run time | 10 minutes |

-continued

| Temperature | Ambient |
|---|---|
| Injection volume | 20 µl |

All results are quoted in area percent.

The invention claimed is:

1. A solid cosmetic composition in the form of an emulsion comprising a dispersed phase of a polar liquid and a continuous phase of a water-immiscible liquid, a solidifying amount of a gellant for the water-immiscible liquid, an emulsifier and a cosmetic active wherein the gellant for the water-immiscible liquid comprises a combination of gellant (i), an N-acyl substituted amino acid amide of formula $A^x$-CO—$R^x$ in which $A^x$ represents the residue of an amino acid amide and $R^x$ represents a branched alkyl group containing from 4 to 12 carbon atoms and gellant (ii), a fibre-forming amido structurant other than N-acyl substituted amino acid amides according to gellant (i) in an effective relative weight ratio.

2. A composition according to claim 1 wherein $A^x$ represents the residue of diamido-substituted glutamic acid or aspartic acid.

3. A composition according to claim 2 wherein $A^x$ represents the residue of diamido-substituted glutamic acid.

4. A composition according to claim 1 wherein each amido substituent in $A^x$ has the formula —CO—NH—$R^z$ in which $R^z$ represents an alkyl group containing from 3 to 6 carbon atoms.

5. A composition according to claim 4 wherein $R^z$ represents a linear alkyl group.

6. A composition according to claim 4 wherein $R^z$ represents butyl.

7. A composition according to claim 1 wherein $R^x$ contains from 5 to 8 carbon atoms.

8. A composition according to claim 7 wherein $R^x$ contains 7 or 8 carbon atoms.

9. A composition according to claim 1 wherein $R^x$ contains a single side chain.

10. A composition according to claim 9 wherein the side chain contains up to 4 carbon atoms.

11. A composition according to claim 1 wherein —CO—$R^x$ is the residue of 2-ethyl-hexanoic acid.

12. A composition according to claim 1 in which gellant (i) is present in a concentration of from 1 to 8% by weight of the composition.

13. A composition according to claim 1 in which gellant (i) is present in a concentration of from 2 to 15% by weight of the water-immiscible phase.

14. A composition according to claim 1 wherein gellant (ii) is selected from gellants (iia) a N-acyl substituted amino acid amide other than gellant (i), and (iib) a cyclodipeptide which satisfies the following general formula:—

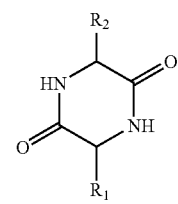

in which one of $R_1$ and $R_2$ represents an alkyl, alkyl ester group and the other represents an alkyl or alkaryl group.

15. A composition according to claim 1 wherein gellant (iia) is an N-acyl substituted amino acid amide of formula $A^Y$-CO—$R^Y$ in which $A^Y$ represents an amino acid amide and $R^Y$ represents a linear alkyl group containing from 9 to 21 carbon atoms.

16. A composition according to claim 14 wherein the weight ratio of gellant (i) to gellant (iia) is selected in the range of from 4:1 to 1:4.

17. A composition according to claim 14 wherein the weight ratio of gellant (i) to gellant (iia) is selected in the range of from 2:1 to 1:2.

18. A composition according to claim 14 wherein $R^Y$ represents undecanyl.

19. A composition according to claim 14 wherein $A^Y$ represents the residue of diamido-substituted glutamic acid.

20. A composition according to claim 14 wherein each amido substituent in $A^Y$ has the formula —CO—NH—$R^Z$ in which $R^C$ represents an alkyl group containing from 3 to 6 carbon atoms.

21. A composition according to claim 14 wherein $R^Z$ represents a linear alkyl group.

22. A composition according to claim 20 wherein $R^Z$ represents butyl.

23. A composition according to claim 14 wherein the proportion of N-acyl amino acid amide gellant (iia) is from 1 to 8% by weight of the composition.

24. A composition according to claim 14 wherein the proportion of N-acyl amino acid amide gellant (iia) is from 2 to 15% by weight of the water-immiscible phase.

25. A composition according to claim 14 in which the combined weight of gellant (i) and N-acyl aminoacid amide gellant (iia) is from 5 to 12% of the composition.

26. A composition according to claim 25 wherein the combined weight of gellant (i) and gellant (iia) is from 6 to 9% of the composition.

27. A composition according to claim 14 wherein the cyclodipeptide (iib) satisfies the formula:—

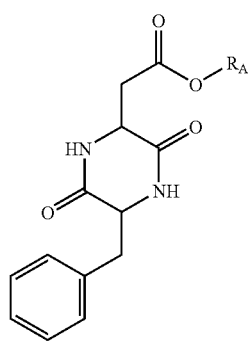

in which $R_A$ represents a carbocyclic or heterocyclic group containing not more than 2 rings.

28. A composition according to claim 27 wherein $R_A$ represents a 6 membered carbocyclic ring that is optionally substituted by 1 to 3 alkyl groups, each independently containing 1 to 3 carbon atoms.

29. A composition according to claim 28 wherein the residue $R_A$ is derivable from thymol or a 3,5-dialkylcyclohexanol.

30. A composition according to claim 26 wherein the cyclodipeptide gellant (iib) is present in a weight ratio to the gellant (i) of from 1:5 to 1:1.

31. A composition according to claim 30 wherein the cyclodipeptide gellant (iib) is present in a weight ratio to the gellant (i) of from 1:4 to 1:1.5.

32. A composition according to claim 31 wherein the cyclodipeptide gellant (iib) is present in a weight ratio to the gellant (i) of from 1:3 to 1:2.

33. A composition according to claim 24 wherein the cyclodipeptide gellant (iib) is present in an amount of from 0.4 to 4% by weight of the composition.

34. A composition according to claim 24 wherein the cyclodipeptide gellant (ii) is present in an amount of from 0.8 to 8% by weight of the water-immiscible phase.

35. A composition according to claim 24 wherein the combined weight of gellant (i) and cyclodipeptide gellant (iib) is from 1.5% to 8% of the composition.

36. A composition according to claim 33 wherein the combined weight of gellant (i) and cyclodipeptide gellant (iib) is from 2.5% to 5% of the composition.

37. A composition according to claim 1 wherein gellant (ii) comprises gellant (iic) cyclohexane substituted by two or three amido groups of formula —$(CH_2)_v$—NH—CO—$R^{111}$ in which $R^{111}$ represents an alkyl group of from 5 to 27 Carbon atoms and v is an integer selected from zero and one.

38. A composition according to claim 37 wherein the cyclohexane is substituted by two amido groups in a 1,2 or 1,3 relationship around the cyclohexane nucleus.

39. A composition according to claim 38 wherein the cyclohexane is substituted by two amido groups in the 1,2 relationship and v=zero.

40. A composition according to claim 37 wherein the cyclohexane is substituted by three aminocarbonyl groups in a 1,3,5 relationship around the cyclohexane nucleus and v=zero.

41. A composition according to claim 1 wherein gellant (ii) comprises gellant (iid) a di or tri carboxylic acid amide, each amido group containing a $C_{1-22}$ substituent.

42. A composition according to claim 1 wherein gellant (ii) comprises gellant (iie), an hydroxystearic acid amide.

43. A composition according to claim 42 wherein gellant (iie) is an amide of 12-hydroxystearic acid.

44. A composition according to claim 42 wherein the amide substituent has a linear alkyl group containing from 3 to 13 carbon atoms.

45. A composition according to claim 37 wherein the total weight of amido-substituted gellant (iic) and the carboxylic acid amide gellant (iid) and the hydroxystearamide gellant (lie) is a minor fraction of the total weight of all gellants (ii) in the composition.

46. A composition according to claim 45 wherein one or more of the gellants (iic) (iid) and (iie) is present in a weight ratio to the gellant (i) of from 1:10 to 1:1.

47. A composition according to claim 36 wherein the amido-substituted gellant (iic) or the carboxylic acid amide gellant (iid) or the hydroxystearamide gellant (lie) is present in an amount of from 0.5 to 4% by weight of the composition.

48. A composition according to claim 1 wherein the water-immiscible continuous phase comprises a silicone oil.

49. A composition according to claim 48 wherein the silicone oil is present in a proportion of from 30 to 80% by weight of the water-immiscible carrier liquid.

50. A composition according to claim 49 wherein the silicone oil comprises a volatile silicone oil.

51. A composition according to claim 1 wherein the continuous phase comprises a water-immiscible monohydric alcohol having a melting point of not higher than 30° C. and a boiling point of higher than 100° C.

52. A composition according to claim 51 wherein the alcohol is a branched aliphatic alcohol containing from 12 to 22 carbon atoms.

53. A composition according to claim 51 wherein the monohydric alcohol is present in a proportion of from 20 to 50% by weight of the water-immiscible liquid.

54. A composition according to claim 1 wherein a benzoic acid ester is present in a proportion of from 0.5 to 50% by weight the water-immiscible liquid.

55. A composition according to claim 54 wherein the benzoic acid ester is a long chain alkyl benzoate, the alkyl group containing on average from 10 to 18 carbon atoms.

56. A composition according to claim 55 wherein the weight proportion of long chain alkyl benzoate in the water-immiscible liquid is from 5 to 30%.

57. A composition according to claim 56 wherein from 0.1 to 4%, by weight of the water-immiscible liquid is benzyl benzoate.

58. A composition according to claim 1 wherein the continuous phase constitutes from 20 to 80% by weight of the composition.

59. A composition according to claim 1 wherein all or part of the cosmetic active is dissolved in the disperse phase.

60. A composition according to claim 59 wherein the cosmetic active comprises a water-soluble antiperspirant or deodorant active.

61. A composition according to claim 60 wherein the antiperspirant or deodorant active comprises an astringent aluminium and/or zirconium salt.

62. A composition according to claim 61 wherein the aluminium or zirconium salt comprises an aluminium chlorohydrate, an aluminium-zirconium chlorohydrate or an aluminium-zirconium chlorohydrate complex.

63. A composition according to claim 59 wherein the cosmetic active is present in a weight proportion of from 25 to 60% of the disperse phase.

64. A composition according to claim 59 wherein the disperse phase comprises from 25 to 85% by weight of water.

65. A composition according to claim 59 wherein the disperse phase comprises from 0.5 to 30% by weight of a water-soluble di or polyhydric alcohol.

66. A composition according to claim 65 wherein the polyhydric alcohol comprises glycerol.

67. A composition according to claim 66 wherein the dihydric alcohol comprises a glycol or glycol ether.

68. A composition according to claim 1 wherein the emulsifier is present at a concentration of form 0.2 to 2% by weight of the composition.

69. A composition according to claim 1 wherein the emulsifier is a dimethicone copolyol.

70. A composition according to claim 1 wherein the disperse phase and the continuous phase have matched refractive indeces.

71. A process for the preparation of a cosmetic composition according to claim 1 comprising the steps of:—
  a1) incorporating into a water-immiscible liquid carrier a structurant which is intended to form a continuous phase one or more gellants as defined in claim 1,
  a2) mixing the liquid carrier with a polar liquid intended to form a disperse liquid phase comprising a cosmetic active in the water-immiscible liquid,
  a3) heating the liquid carrier or a mixture containing it to an elevated temperature at which the gellant is dissolved or dispersed in the water-immiscible liquid carrier
  a4) introducing an emulsifier into either the water-immiscible liquid carrier or the polar liquid
  steps a1) a2) a3) and a4) being conducted in any order followed by:
  b1) introducing the mixture into a mould which preferably is a dispensing container, and then
  c1) cooling or permitting the mixture to cool to a temperature at which the liquid carrier is solidified.

72. A process according to claim 71 wherein gellant (i) is dissolved in a first fraction of the water-immiscible liquid and gellant (ii) is dissolved in a second fraction of the water-immiscible liquid and the fraction containing dissolved gellant (i) is mixed with a mixture obtained in step a2 of the second fraction and the polar liquid.

73. A process according to claim 72 wherein the first fraction comprises a water-immiscible monohydric alcohol that is liquid at 20° C. and boils at above 100° C.

74. A cosmetic method for inhibiting or controlling perspiration and/or malodour generation comprising applying topically to human skin an effective amount of a cosmetic composition according to claim 57.

* * * * *